DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED SEPTEMBER 3, 1974

926 O.G. 9

T926,002

THERMAL CHLORINATION OF BUTADIENE-1,3

Kenneth C. Eberly and Edward Leo Kay, Akron, Ohio, assignors to The Firestone Tire & Rubber Company, Akron, Ohio

Continuation of application Ser. No. 177,128, Sept. 1, 1971, which is a continuation of application Ser. No. 799,962, Feb. 17, 1969. This application Nov. 17, 1972, Ser. No. 307,731

Int. Cl. C07c *21/20*

U.S. Cl. 260—655

No Drawing. 7 Pages Specification

Butadiene-1,3 is thermally chlorinated in the vapor phase to produce 1-chlorobutadiene-1,3. The butadiene-1,3 is brought into contact with chlorine, in the presence of an inert diluent, in a reaction zone at a temperature of from 300° to 600° C., preferably from 350° to 550° C. From five to 20 moles of butadiene-1,3 are present per mole of chlorine, and from five to 25 moles of the inert diluent per mole of chlorine. The reaction products are removed from the reaction zone and cooled. The 1-chlorobutadiene-1,3 portion is then separated from the reaction products. Unreacted butadiene-1,3 and the inert diluent may be recycled. The reaction is preferably performed continuously.